(12) United States Patent
Dehmeshki et al.

(10) Patent No.: US 12,165,309 B2
(45) Date of Patent: Dec. 10, 2024

(54) DEFORMITY EDGE DETECTION

(71) Applicant: Fuel 3D Technologies Limited, Oxford (GB)

(72) Inventors: Jamshid Dehmeshki, Oxford (GB); Adeala Zabair, Oxford (GB); Leo Navarro, Oxford (GB); George Thaw, Oxford (GB)

(73) Assignee: FUEL 3D TECHNOLOGIES LIMITED, Oxfordshire (GB)

(*) Notice: Subject to any disclaimer, the term of this patent is extended or adjusted under 35 U.S.C. 154(b) by 859 days.

(21) Appl. No.: 17/252,229

(22) PCT Filed: May 30, 2019

(86) PCT No.: PCT/GB2019/051485
§ 371 (c)(1),
(2) Date: Dec. 14, 2020

(87) PCT Pub. No.: WO2019/239106
PCT Pub. Date: Dec. 19, 2019

(65) Prior Publication Data
US 2021/0264593 A1    Aug. 26, 2021

(30) Foreign Application Priority Data
Jun. 14, 2018   (GB) .................................... 1809768

(51) Int. Cl.
*G06T 7/64* (2017.01)
*A61B 5/00* (2006.01)
(Continued)

(52) U.S. Cl.
CPC ............ *G06T 7/0012* (2013.01); *A61B 5/004* (2013.01); *A61B 5/444* (2013.01); *A61B 5/7264* (2013.01);
(Continued)

(58) Field of Classification Search
CPC ..... A61B 2503/40; A61B 5/004; A61B 5/444; A61B 5/7264; G06F 18/2431;
(Continued)

(56) References Cited

U.S. PATENT DOCUMENTS

2011/0196524 A1* 8/2011 Giasson ................ B33Y 50/00
                                                         700/118
2013/0018271 A1   1/2013 Hani et al.
(Continued)

OTHER PUBLICATIONS

Fulgencio Navarro, "Accurate Segmentation and Registration of Skin Lesion Images to Evaluate Lesion Change," Mar. 6, 2019, IEEE Journal of Biomedical and Health Informatics, vol. 23, No. 2, Mar. 2019,pp. 501-507.*
(Continued)

*Primary Examiner* — Omar S Ismail
(74) *Attorney, Agent, or Firm* — Thomas | Horstemeyer, LLP

(57) ABSTRACT

A method for estimating a region associated with a deformity on a surface portion of the skin of a mammal, the method comprising capturing a three-dimensional image of the surface portion to produce first data, the first data comprising depth data, and generating second data from the first data. The second data comprises curvature data. The method further comprises combining the first data and the second data to produce third data, and performing region growing on the third data.

18 Claims, 8 Drawing Sheets

(51) Int. Cl.

| | | |
|---|---|---|
| *G06F 18/2431* | (2023.01) | |
| *G06T 3/40* | (2024.01) | |
| *G06T 7/00* | (2017.01) | |
| *G06T 7/11* | (2017.01) | |
| *G06T 7/12* | (2017.01) | |
| *G06T 7/174* | (2017.01) | |
| *G06T 7/187* | (2017.01) | |
| *G06T 7/40* | (2017.01) | |
| *G06T 7/50* | (2017.01) | |
| *G06T 7/62* | (2017.01) | |
| *G06T 19/20* | (2011.01) | |

(52) U.S. Cl.
CPC ............ *G06F 18/2431* (2023.01); *G06T 3/40* (2013.01); *G06T 7/11* (2017.01); *G06T 7/12* (2017.01); *G06T 7/187* (2017.01); *G06T 7/40* (2013.01); *G06T 7/50* (2017.01); *G06T 7/62* (2017.01); *G06T 7/64* (2017.01); *G06T 19/20* (2013.01); *A61B 2503/40* (2013.01); *G06T 7/174* (2017.01); *G06T 2207/10048* (2013.01); *G06T 2207/20084* (2013.01); *G06T 2207/30088* (2013.01); *G06T 2207/30096* (2013.01); *G06T 2219/2021* (2013.01); *G06V 2201/03* (2022.01); *G06V 2201/032* (2022.01)

(58) Field of Classification Search
CPC ........... G06T 19/20; G06T 2207/10028; G06T 2207/10048; G06T 2207/20084; G06T 2207/30088; G06T 2207/30096; G06T 2219/2021; G06T 3/40; G06T 7/0012; G06T 7/11; G06T 7/12; G06T 7/174; G06T 7/187; G06T 7/40; G06T 7/50; G06T 7/62; G06T 7/64; G06V 2201/03; G06V 2201/032

See application file for complete search history.

(56) References Cited

U.S. PATENT DOCUMENTS

| | | | | |
|---|---|---|---|---|
| 2014/0067679 | A1* | 3/2014 | O'Reilly | G06Q 20/40145 705/44 |
| 2014/0288463 | A1* | 9/2014 | De Waele | A61B 5/4542 600/593 |
| 2015/0326842 | A1* | 11/2015 | Huai | H04N 9/73 348/223.1 |
| 2016/0310083 | A1* | 10/2016 | Wang | A61B 5/0073 |
| 2016/0321797 | A1* | 11/2016 | Richard | G06T 7/0006 |
| 2017/0039704 | A1* | 2/2017 | Kasmi | A61B 5/444 |
| 2017/0124709 | A1* | 5/2017 | Rithe | G06V 10/56 |
| 2017/0193659 | A1 | 7/2017 | Wang et al. | |
| 2018/0103892 | A1* | 4/2018 | Kaur | G06T 7/0012 |
| 2023/0222750 | A1* | 7/2023 | Querbes | G06T 7/70 345/420 |

OTHER PUBLICATIONS

Roberta B. Oliveira,"A computational approach for detecting pigmented skin lesions in macroscopic images," May 12, 2016,vol. 61, Nov. 1, 2016, pp. 53-60.*
Mercedes Filho,A Review of the Quantification and Classification of Pigmented Skin Lesions: From Dedicated to Hand-Held Devices,Sep. 28, 2015,Journal of Medical Systems vol. 39, Article No. 177 (2015) ,pp. 1-5.*
Maurício Pamplona Segundo,"Automatic Face Segmentation and Facial Landmark Detection in Range Images," Sep. 15, 2010, IEEE Transactions ON Systems, Man, and Cybernetics—Part B: Cybernetics, vol. 40, No. 5, Oct. 2010,pp. 1319-1327.*
Khaled Taouil,"A New Automatic Approach for Edge Detection of Skin Lesion Images," Oct. 16, 2006,2006 2nd International Conference on Information & Communication Technologies,pp. 212-218.*
JA Delgado San Martin,"Non-invasive 3D time-of-flight imaging technique for tumour volume assessment in subcutaneous models," Dec. 5, 2014,Sage Journals Home,vol. 49, Issue 2,pp. 168-170.*
M. Di Luca, "Inconsistency of perceived 3D shape," May 5, 2010, Vision Research 50 (2010) , pp. 1519-1527.*
Jessica P. Miller, "Gradient-Based Algorithm for Determining Tumor Volumes in Small Animals Using Planar Fluorescence Imaging Platform," Mar. 1, 2016, Tomography,vol. 2(1),2016,pp. 17-24.*
Hani et al., "In Vivo 3D Thickness Measurement of Skin Lesion," Apr. 5, 2011, 2010 IEEE EMBS Conference on Biomedical Engineering & Sciences (IECBES 2010), Kuala Lumpur, Malaysia, Nov. 30-Dec. 2, 2010,pp. 155-159.*
Rahul Pal et al. ,"Remodeling of the Epithelial-Connective Tissue Interface in Oral Epithelial Dysplasia as Visualized by Noninvasive 3D Imaging," Aug. 14, 2016, Cancer Res (2016)76(16),pp. 4637-4644.*
M. Hani Ahmad Fadzil et al. , "3D surface roughness measurement for scaliness scoring of psoriasis lesions," Aug. 15, 2013, Computers in Biology and Medicine 43(2013),pp. 1988-1997.*
Combined Search and Examination Report, GB Application 1809768. 3, dated Dec. 13, 2018 (7 pages).
International Preliminary Report on Patentability, International Patent Application PCT/GB2019/051485, mailed Sep. 18, 2020 (17 pages).
Franke, Beate, et al., "A 3D scanning technology to measure subcutaneous tumour volume. Are callipers obsolete?" Quantitative Biology Discovery Sciences, May 11, 2018.
Luca, M. Di, et al., "Inconsistency of perceived 3D shape," Vision Research 50, (2010), pp. 1519-1531.
Smith, Andrew, "Are Calipers Obsolete? 3D Subcutaneous Tumor Scanning and the Lab of the Future," Jan. 26, 2018, retrieved from the internet on Aug. 5, 2019, https://www.laboratoryequipment.com/article/2018/02/are-calipersobselete.
San Martin, JA Delgado, et al., "Non-invasive 3D time-of-flight imaging technique for tumour volume assessment in subcutaneous models," Laboratory Animals, vol. 49(2), (2015), pp. 168-171.

* cited by examiner

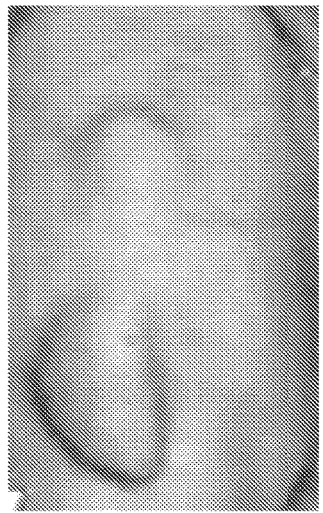
Fig. 7(a)
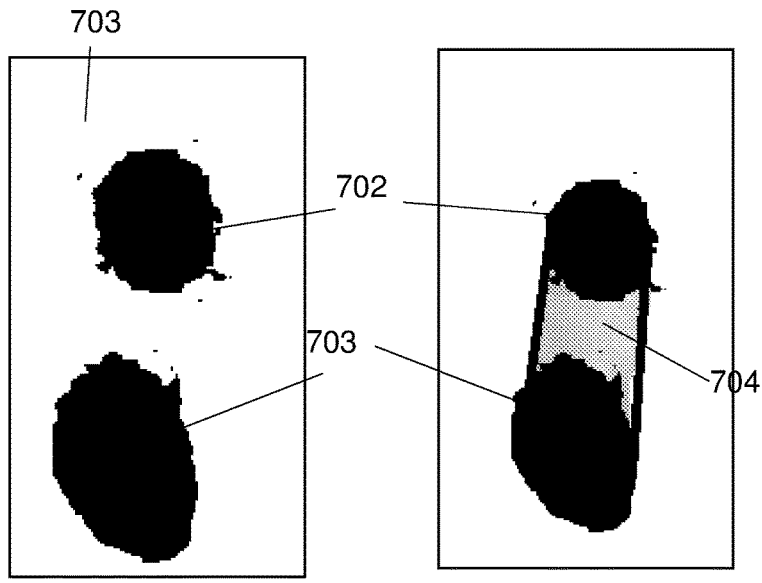
Fig. 7(b)
Fig. 7(c)
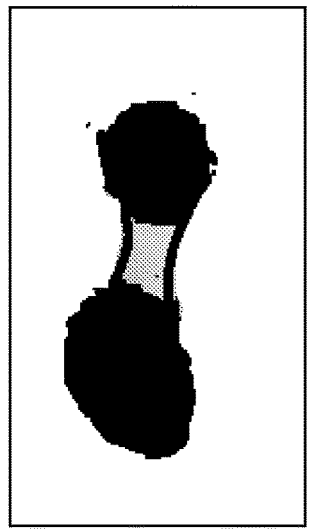
Fig. 7(d)
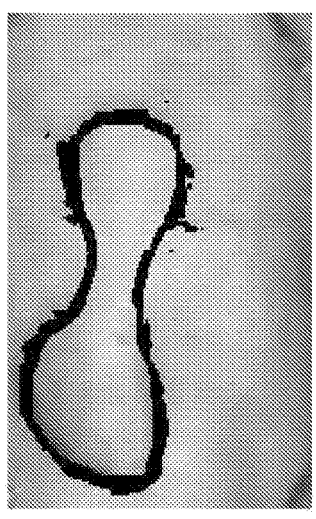
Fig. 7(e)

DEFORMITY EDGE DETECTION

CROSS-REFERENCE TO RELATED APPLICATION

This application is the 35 U.S.C. § 371 national stage application of PCT Application No. PCT/GB2019/051485, filed May 30, 2019, where the PCT claims priority to and the benefit of, GB Patent Application No. 1809768.3, filed Jun. 14, 2018, both of which are herein incorporated by reference in their entireties.

FIELD OF THE INVENTION

The present invention relates to a method for detecting regions associated with a deformity on a surface portion of the skin of an animal, especially a mammal, such as a rat or other rodent. It further relates to an imaging system capable of performing the method.

BACKGROUND OF THE INVENTION

It is known that skin deformities such as those caused by tumours on or under the skin of laboratory animals such as rats or other mammals can be imaged using 3D imaging systems. These types of systems are intended to replace or be used in conjunction with traditional calliper techniques where a human laboratory worker manually scruffs and measures the size and other characteristics of a deformity using callipers. A system which determines if a mammal has been correctly scruffed before a 3D imaging step is performed on the mammal is described in PCT/GB2017/053714. However, It is known that calliper techniques do not always produce consistent data due to the inherent human error present in such techniques.

Deformities may be classified according to how they present themselves on the skin surface. For example, a tumour consisting of a single, regularly shaped lump situated immediately under the skin will present itself on the surface of the skin as a single, regularly shaped, raised peak. In contrast, more complex tumours may show two, or less commonly three, or more peaks on the surface of the skin depending on their shape.

Known 3D imaging systems use laser imaging to generate a 3D image of the region of mammal skin being imaged. The 3D image includes a depth map (also known as a z-map) which, in a Cartesian coordinate system, generates a Z coordinate indicating the height or depth of the surface being measured. From the depth map, a curvature map may be calculated using, for example, principle curvature, Gaussian curvature, mean curvature, normal section, and/or other known surface curvature calculation techniques. Edge detection may be then performed on the curvature map to find the edge of the deformity. The term map as used herein refers to a data set composed of data points, each data point associated with a pixel on an image. Thus a depth map comprises depth data identifying individual pixels and a depth associated with each pixel. A curvature map comprises curvature data identifying individual pixels and a curvature associated with each pixel.

A known image segmentation technique is region growing. In region growing, an initial seed point pixel(s) is selected and compared to its neighbouring pixels based on, for example, average intensity, variance, colour, or other region membership criteria. If the seed point pixel's neighbours meet the same region membership criteria as the seed point pixel, they are added to the same region. If not, they are added to a different region, such as a background region. The process is iterated until the whole image has been segmented into different regions.

One type of region growing is known as the level-set method. The level-set method enables numerical calculations involving curves and surfaces on a fixed Cartesian grid to be performed without having to parameterize the curves and surfaces. Instead, an auxiliary function p called the level-set function is used to represent a closed curve F (which may be the shape of the boundary of an object). F is represented as the zero-level-set of p by:

$$\Gamma=\{(x,y)|\varphi(x,y)=0\}$$

and the level-set method manipulates $\Gamma$ implicitly through $\varphi$. Informally, the level-set method starts with an initial guess of an edge curve, which is iterated by applying shrinking or growing operations until termination conditions are reached and the iterations are stopped. A termination condition may be that the level set convergence speed meets a predetermined value, indicative of a low gradient.

Once the edge of a deformity or the region associated with a deformity has been estimated, the size and other characteristics of the deformity can be extracted. The term size may include information from which the deformity's diameter, height, volume and shape can be determined.

The term deformity as used herein may include any deformity which changes the three-dimensional shape of the animal's skin, such as a growth and/or cavity. In the case of a cavity, it is to be understood that the cavity dips into the surface of the skin, rather than rises above it.

SUMMARY OF THE INVENTION

The inventors have noticed that algorithms which use region growing techniques such as the level-set method to detect edges or regions associated with a deformity only perform well on single peak deformities. Where a deformity has two, three, or more peaks, region growing algorithms are prone to erroneously reaching the algorithm termination conditions too early (i.e. conditions where there is no or only minimal change in output values over N number of iterations), and thus underestimating deformity size. This is particularly the case at local minima such as flat regions surrounding saddle points between two or more peaks. The curvature in these flat regions is close to or at zero and the change region growing algorithm output values over N number of iterations is small. Region growing algorithms are thus prone to incorrectly deeming the termination conditions to have been reached. This results in a consistent underestimation of deformity size. Further, region growing methods are prone to segmentation leakage in the above described flat regions between two or more peaks, as the pixels in these regions are more likely to be similar in appearance to the pixels of the background healthy skin, thus causing the region growing algorithms to erroneously associate them with a background region rather than with the deformity. Whilst region growing algorithms can be modified to be less aggressive (i.e. more conservative) in classifying an edge or region, this instead results in a consistent overestimation in deformity size. In particular, region growing algorithms which have been modified to be less aggressive do not consider the termination conditions to have been reached even when the global minimum (i.e. healthy surrounding skin) has been reached, and thus do not terminate, thus resulting in a constant overestimation in size. Conversely, curvature may be high in locations which are not associated with deformities (e.g. where there are hairs or temporary wrinkles on the skin due to how the animal is held).

In general terms, the present invention proposes two techniques which can be used separately or together to more accurately detect the boundaries of a region of skin associated with multi-peaked deformities (i.e. deformities).

The first technique is to perform data fusion between at least two different data sets characterizing a plurality of locations on the skin. In particular, at least one, or at least two, of the data sets may by ones which characterize the shape of the skin surface, such as a depth map obtained from the 3D image and/or a calculated curvature map. In other possibilities, one of the data sets may characterize the normal direction of different portions of the skin (or a departure of the normal direction from a normal direction of a respective point on a model of the skin surface). Optionally, one or more of the data sets may be data set which does not describe the shape of the surface of the skin, such as a data set specifying colours of points on the skin surface, and/or a data set specifying temperatures of points on the skin surface.

Let us consider the case that the data sets are respectively depth data and curvature data. As described above, one of the reasons why level-set algorithms terminate early at flat regions between peaks is that the curvature in these regions is close to zero and the change in level-set algorithm output values over N iterations is small. For a single peak deformity, an almost zero curvature and a small change in region growing algorithm output values over N iterations correctly indicates that the flat surface of the surrounding healthy skin has been reached by the algorithms and that the boundaries of the region of skin associated with the single peak deformity has been found. However, for a multi-peak deformity, a small change in region growing algorithm output values and almost zero curvature does not necessarily mean zero depth relative to the surrounding healthy skin and/or that the boundary of a region associated with the deformity has been reached. Indeed there is a great deal of information in the curvature map which cannot be inferred from the depth map alone, and vice versa. By fusing the depth map data and the curvature map data, the curvature values are modified in the data fusing process in proportion to their depth (in this case height above the healthy, surrounding skin). If region growing techniques such as, but not limited to, the level-set method are then performed on the fused data, the algorithms will no longer terminate in the flat regions between peaks, as the data values corresponding to these points will have been changed in the fusion process and should no longer correspond to the lowest values in the fused data set and thus no longer have small changes in region growing algorithm output values over N iterations. This increases the likelihood that the region growing algorithms, such as the level-set method, correctly determine when termination conditions have been reached. If a region growing method is used on the fused data, pixels of the flat regions of the deformity and the surrounding healthy skin which previously would have appeared similar no longer do, as their values are modified in proportion to their associated depth, which is different for the flat regions of the deformity and the surrounding healthy skin. Effectively, the data fusion process emphasises the data indicative of the boundary of a region, and decreases the importance of the data not indicative of the boundary during the region growing stage.

In one example, the fusion of two data sets may describe a process of deriving, for each a plurality of points on the surface, from a first data value describing the point in a first of the data sets, and a second data value describing the point in a second of the data sets, at least one third value describing the point. The fusion of the first and second data values to obtain the third value(s) may be performed using a function which is the same for all of the plurality of points on the skin.

The second technique is to split the data associated with a single multi-peak deformity into separate data sets each associated with one of the single peaks. Region growing methods, such as the level-set method, which work well on single peak deformities, may then be performed on the split data to accurately determine the edges of each of the single peaks or the regions associated therewith. The single peak edge positions or the regions associated with the individual peaks may then be combined to provide overall edge positions of and/or a single region associated with the full, multi-peak deformity which is more accurate than if region growing methods such as the level-set method had been performed on the multi-peak deformity without splitting the data. By splitting the multi-peak deformity data set into multiple single peak deformity data sets, advantage can be taken of the level-set or region growing method's good suitability for use on single peak deformities.

The first technique, hereinafter described as data fusing (where the term fusing, may alternatively be referred to generally as combining), and the second technique, hereinafter described as peak splitting, may be performed alone or together. It is envisaged that when the two techniques are performed together, data fusing will be performed before peak splitting. For example, the depth map and curvature maps may be fused first before peak splitting takes place. Splitting the fused data will then produce a fused data set for each peak. The level-set method or other region growing method may then be performed on each of the fused data sets, before the results are combined to obtain the edge position of or region associated with the multi-peak deformity.

In some embodiments, peak splitting may involve the following steps. Initially, peak positions are located on the curvature map and/or depth map and identified by their (x,y) coordinates in a Cartesian coordinate system, corresponding to, for example, pixel position. Any other suitable coordinate system may also be used, such as for example, polar, cylindrical, and/or spherical coordinate systems. The peak positions may be identified using any suitable feature detection techniques, for example, by using extremes such as maxima or minima in the depth map. Region growing is then performed using e.g. one or more pixel coordinates of the peak positions as seed points or regions to segment the image into different regions associated with each peak.

In some embodiments, Otsu's method is used to determine the seed points or regions for the initial region growing stage. Otsu's method is a thresholding technique in which an assumption is made that pixels either belong to the foreground or background, and an optimal threshold is that in which a combined spread (i.e. intra-class variance) is either minimal or maximal. The inventors have realised that performing Otsu's method solely on the depth map or solely on the curvature map results in prohibitively large numbers of possible starting seed regions. In particular, skin folds, and other surface imperfections are categorised as being in the foreground using Otsu's method. However, when data fusing is performed to generate a third, fused data set, and Otsu's method is performed on the fused data set, the inventors unexpectedly found that Otsu's method correctly associated pixels in the peak regions as belonging to the foreground, and correctly associated other surface imperfections with the background. The inventors thus found that Otsu's method performed on the fused data set provided much higher accuracy seed regions for subsequent region growing as used during peak splitting.

During subsequent region growing, each pixel will be assigned to one of the seed regions or to the background.

An alternative image segmentation methods may also be used to generate initial seed regions. These methods include, but are not limited to, other thresholding and clustering methods, compression-based methods, histogram-based methods, parametric methods, partial differential equation-based methods, variational methods, graph partitioning methods, watershed transformation methods, and/or model based segmentation methods. These methods may be performed automatically, or if required, with the assistance of user input.

In some embodiments, it is envisaged that initial seed region generation may be performed by a neural network, trained on a sufficiently large dataset of correctly segmented images. The term neural network as referred to herein includes, for example, convolutional networks capable of performing deep learning. In particular, it is envisaged that fully convolutional networks (i.e. a convolutional neural network where the last fully connected layer is substituted by another convolutional layer with a large receptive field, and ended with a softmax layer) are particularly suited for peak splitting performed using deep learning. However, any suitable neural network architecture which is capable of image segmentation may also be used. An advantage of performing image segmentation with a neural network is that overcomes the need to manually set the parameters used to perform the segmentation as the network will learn these itself.

Once all of the pixels have been assigned to a region, a plurality of the regions which are associated with the individual peaks may be combined. The term combining refers to any region merging technique in which two distinct regions are combined to produce a single region having a continuous border. That is, a contiguous region. This may be achieved by generating a convex hull around the edges of the peaks, thus defining a contiguous region including the peaks, and then performing region shrinking on this region. Region shrinking iteratively takes a starting set of pixels around the edges of one region and assigns them to an adjacent region if predetermined region membership criteria are met, thus shrinking the first region. As described above, it is envisaged that the starting set of pixels may be determined by a convex hull model defined between the two or more peak regions. A convex hull model in this case defines the smallest curve which encloses all of the pixels between the outermost pixels of the individual peak regions. The pixels which are found to be within this curve are used as a starting set of pixels for region shrinking. As region shrinking is performed, each pixel is compared to its neighbours to determine whether or not the pixel meets the predetermined deformity region membership criteria. If it does not, the pixel is assigned to the background region. If it does, then then the pixel is associated with the deformity. Any other suitable alternative to region shrinking of a convex hull seed region may also be used. For example, instead of using a convex hull, a thin band of pixels may be taken between the centres of each of the peaks. This band my then be grown outwards (i.e. using region growing) until stopping criteria are met. Thus, the combining step may comprise refining a boundary of contiguous region which is a convex hull or other shape, using for example region growing or shrinking, or any other suitable bridging technique.

In some embodiments, it is envisaged that the regions may be combined using convolutional neural networks capable of performing deep learning. In particular, a convolutional network trained on a suitably large dataset would be able to combine the regions associated with the separate peaks to create a composite image indicating where the boundaries of the multi-peak deformity region are. The output of the above described peak splitting technique provides a more accurate estimate of the boundaries of a multi-peak deformity region than is possible to obtain without peak splitting.

Where a convolutional neural network is used to carry out any steps of the above described methods, one or more graphics processing units (GPU) or tensor processing units (TPU) may be used alone or in conjunction with the processor of a 3D imaging system to carry out the machine learning aspects of the calculations. The GPUs and/or TPUs may be contained within the 3D imaging system itself, or in the cloud so as to provide computing resources which are scalable based on user requirements.

It is envisaged that in some instances, where the initial seed region generation step, and subsequent region growing step, result in very close or contiguous peak regions, or indeed partially overlapping peak regions, it may not be necessary to perform a separate step of refining the boundary of the convex hull or other shape such as a pixel band. In particular, if the initial region for each of the individual peaks results in a single shape encompassing the centre positions of both peaks, then computing resources can be saved by simply taking the results of the initial region growing step as the output of the algorithm. When this happens, the region growing algorithms are deemed to have correctly detected that the deformity was a single, multi-peaked deformity and thus did not terminate prematurely.

In some instances, the initial seed region generation and subsequent region growing of individual peaks may result in one or more peak regions being found to be entirely within another region. This may be a result of a region growing algorithm having terminated prematurely, and the adjacent region being identified as a second peak, even though both regions should have been identified as being part of the same peak. In such instances, the peak found to be within the region of another peak may be rejected. This may be performed automatically as part of the algorithms, or manually by user input.

Note that deformities are often imaged with some degree of knowledge as to whether or not they are part of e.g. a single tumour. For example, in the case of a tumour which is the result of an injection of a chemical and/or biological agent into the animal, it may be assumed that all deformity is due to a single tumour at that location. Thus, the present method may, in such cases, be designed to assume that all peaks/troughs identified are part of a single deformity.

The technique of data fusing will now be described in general terms. In some embodiments, data fusing may involve the following steps. Initially, the depth map (produced using the 3D imaging system) is converted into a curvature map, using, for example, Gaussian curvature, principle curvature, mean curvature, normal section, and/or other known surface curvature calculation techniques.

Once the depth map and curvature map have been produced, each data point on the curvature map is fused with its associated data point on the depth map. It is envisaged that this may be achieved by, for example, using a function such as $((a*curvature)+(b*depth))^2$ on the data points associated with each pixel coordinate to generate the fused data set, where the values "a" and "b" are weight constants. In other embodiments the function may instead be, for example, the multiplication of each curvature map data point by its associated depth map data point so as to change its value in proportion to the associated depth map value. In further embodiments, either the curvature or depth may be weighted more heavily than the other. This can be done by an appropriate selection of a and b. Alternatively or additionally, it may be done by using one of the following functions: $((a*curvature)^2+(b*depth))^2$ or $((a*curvature)+(b*depth)^2)^2$.

The fused data set which is produced with data fusing is labelled hereinafter as F.

Where region growing is used to determine the boundaries of deformities, it is envisaged that the region membership criteria are to be based on the fused data set F, rather than on the depth map or curvature map alone.

The effect of data fusing is set out as follows.

Data points where the curvature value is low but the depth value is high (e.g. a flat region on the deformity), will have an increased value in the fused data set F compared to the corresponding curvature map data points. An increased value in this context reduces the chance that the region growing algorithms will determine that a boundary of the deformity is at a flat region between peaks and terminate there. This minimises underestimation in deformity size. The increased value in the fused data set F results in a greater difference (effectively an enhanced "contrast" in fused data set values, where the term contrast is used to mean a size of a difference between data values) against pixels of the healthy surrounding. This ensures the pixel is more likely to be assigned to a deformity region rather than a background region.

Data points where the curvature value is high but the depth value is low (e.g. folds in the skin of the mammal adjacent the grown which do not form part of the deformity) will have a lowered value in the fused data set F compared to the corresponding curvature map data points. A lowered value in this context reduces the chance that the region growing algorithms will determine that the skin fold or similar shapes outside of the deformity are mistakenly classified to be within the edge of the deformity. This minimises overestimation in deformity size. The lowered value in the fused data set F is closer to the values of the surrounding healthy skin resulting in a higher chance that a pixel is correctly assigned to a background region rather than a deformity region.

Data points where both the curvature value and depth value are low (e.g. surrounding healthy skin) will have an even lower value in the fused data set, reducing the chance that the level-set algorithm will determine that the surrounding healthy skin is classified to be within the deformity edges. This minimises overestimation in deformity size. The lowered value in the fused data set F again effectively enhances the "contrast" against the values associated with the deformity regions resulting in a higher chance that a pixel is correctly assigned to a background region rather than a deformity region.

Data points where both the curvature value and depth value are high (e.g regions immediately at and around the tops of the peaks) will have an even higher value in the fused data set compared to the corresponding curvature map data points, reducing the chance that the region growing algorithms will miss one or more peaks of a multi-peak deformity. This minimises underestimation in deformity size The increased value in the fused data set F again effectively enhances the "contrast" available for use by the region growing algorithm.

As described above, the data fusing process artificially increases or decreases the value at each point in the fused data set F relative to the other points, based on depth values.

Thus, where a level-set method algorithm termination condition is that the level set convergence speed is slow i.e. the curvature has remained below a specified value for N iterations, and where a previously low curvature value has been multiplied by a high depth value (e.g. at a flat region between peaks) to produce a higher value, the algorithm will no longer find that the curvature value is below the specified value so will not terminate early. In contrast, where a previously low curvature value has been multiplied by a low depth value (e.g. at or beyond the edges of the deformity), the value will remain low. The algorithm will continue to find that the curvature has remained below the specified value for N iterations so will correctly terminate at the actual edges of the deformity.

Similarly, where other region growing techniques are used, the region membership criterion based on the fused data set F effectively has an enhanced contrast as compared to the curvature map or depth map alone. The enhanced contrast reduces the number of pixels which are incorrectly assigned.

Together, the above described effects simultaneously reduce the change of overestimation and underestimation of deformity size, and of assigning pixels to the incorrect regions. It is not possible to obtain a similar benefit only through adjustments of the aggressiveness of the level-set or region growing algorithms, which can only be adjusted to either overestimate, or underestimate deformity size.

An unexpected advantage of data fusing will now be described. As described above, a number of techniques may be used to calculate the curvature map from the depth map. As many of these techniques are computationally expensive, the inventors have found that it is efficient to downsample the depth map (i.e. reduce its pixel resolution using e.g. a multi-scale approach) before calculating the curvature map. If the depth map is based on an image having a pixel resolution of 1024×1024, it may be downsampled using a multi-scale approach any number of times so as to balance computational efficiency with information loss. For example, the depth map may be downsampled to 512×512, 256×256, 128×128, or 64×64 pixels (or indeed to any other resolutions), before the curvature map is generated. After the curvature map has been generated, it may be upsampled back to the resolution of the original depth map. A curvature map calculated from a downsampled depth map will, under normal circumstances, be less accurate than a curvature map calculated from a higher resolution depth map as some of the higher resolution information is lost during downsampling. This is normally true even where the curvature map has been upsampled back to the original resolution size. The information sacrifice is often deemed necessary in practice so as to reduce computing resources required to perform the calculation, and/or to speed up calculation times.

The inventors have unexpectedly found that, when a curvature map calculated from a downsampled depth map (i.e. where some information loss is expected) is fused with the full resolution depth map (i.e. not in a downsampled state) afterwards, the effect of information loss from the downsampling is reversed and the accuracy of the subsequent level-set method or region growing method performed on the fused data set F is improved compared to the accuracy of the level-set method or region growing method performed on a non-fused data set. As data fusing is computationally very cheap compared to the calculations required to generate a curvature map from a high resolution depth map, the additional resources required to perform the data fusing step are negligible compared to computing a full resolution curvature map. This results in a reduction in computational resources required to achieve the same degree of accuracy as the curvature map can be calculated from a downsampled depth map (which is more efficient) without a significant reduction in accuracy.

In particular, where data fusing is used, the inventors have found that a 1024×1024 resolution depth map may be downsampled to a 128×128 resolution depth map prior to calculating the curvature map (in this case using Gaussian curvature techniques) with almost no loss of accuracy in the subsequent edge detection calculation. Similar computational efficiencies may be gained for other degrees of downsampling (e.g. to 512×512, 256×256, 64×64 resolutions). Although it is advantageous to perform the above described downsampling, it is not needed to obtain the above described other advantages of the invention. In particular, the above described effects of simultaneously minimising under and over estimation of deformity sizes, and of improving deformity boundary accuracy through peak splitting, may be achieved without any downsampling.

Although both peak splitting and data fusing have been described using the level-set method as an example of a region growing method. The same advantages are realised in connection with other region growing techniques used in image processing, including edge detection techniques such search-based and zero-crossing based methods, first and second order based methods, and any methods which are prone to over and under estimations as a result early algorithm termination.

The inventors have also realised that a significant computational efficiency gain can be made by realising that, once a peak has been detected, regions surrounding the peak which have at least a specified percentage of the height of the peak must be part of the deformity, thus enabling an initial seed region for region growing to be pre-set to have a minimum distance from the peak, and thus enabling a greater sized starting region to be used for region growing. One reason this is possible in the field of deformity detection is that a detectable deformity will have always have a minimum size. The inventors have found in particular that any region surrounding the peak which is 70% of the peak height is very likely to belong to a deformity. Thus, using the depth map, the boundary of the seed region may initially be set to include any pixel coordinates which have a height greater than approximately 70% of the peak's height. This is computationally efficient as the starting point for the level-set method and other region growing algorithms are set to already include a region corresponding to 30% worth of height of the deformity. The inventors envisage that other percentage values are also feasible and may be determined based on the type of deformity which is to be detected.

An advantageous use of the invention is in laboratory studies of tumour deformity in rats and mice. In particular, tumour volume is a key piece of data in such studies. Tumour volume is highly dependent on the positions of the boundaries of the tumour. As such, the invention provides a means of estimating tumour boundary position more accurately and thus improves the accuracy of tumour volume estimations.

The invention may be expressed in terms of a method carried out by a user using a 3D imaging system (which obtains a 3D image using, for example, stereoscopy and/or photometry), or as a method performed by the 3D imaging system itself, for example, under control of a processor according to program instructions, which may be stored in non-transitory form on a tangible data storage device.

BRIEF DESCRIPTION OF THE DRAWINGS

An embodiment of the invention will now be described for the sake of example only with reference to the following figures in which:

FIGS. 7(a)-(e) are images of the deformity of FIG. 1(c) at different stages of being processed according to an embodiment of the present invention.

DETAILED DESCRIPTION OF THE EMBODIMENTS

Figure 1A:
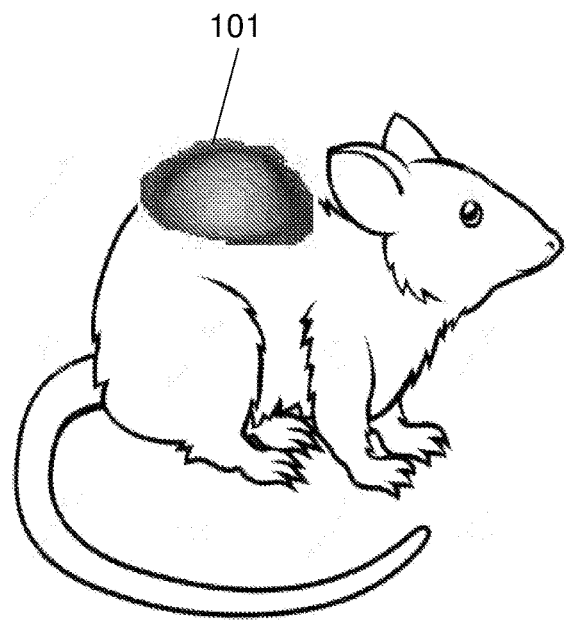
FIGS. 1(a)-(c) are diagrams showing a mammal with a deformity that presents itself respectively as a single peak shape, a multi peak shape, and a double peak shape on the skin surface.

FIG. 1(a) shows diagrammatically how a single peak deformity 101 might present itself on the skin surface of a mammal, such as a rat or mouse (but it may be another mammal, such as a human being). The deformity 101 has a well-defined edge with a single peak.

Figure 1B:
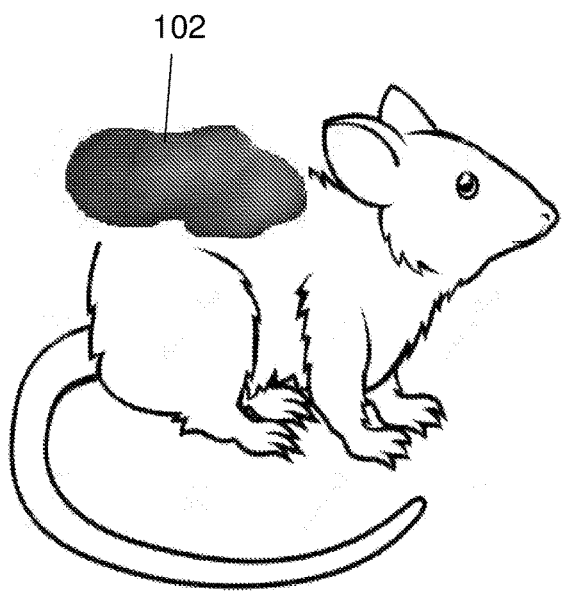

FIG. 1(b) shows diagrammatically how a multi-peak deformity 102 might present itself on the skin surface of a mammal, such as a rat or mouse. The edge of the deformity 102 is not as well-defined and there are a number of peaks.

Figure 1C:
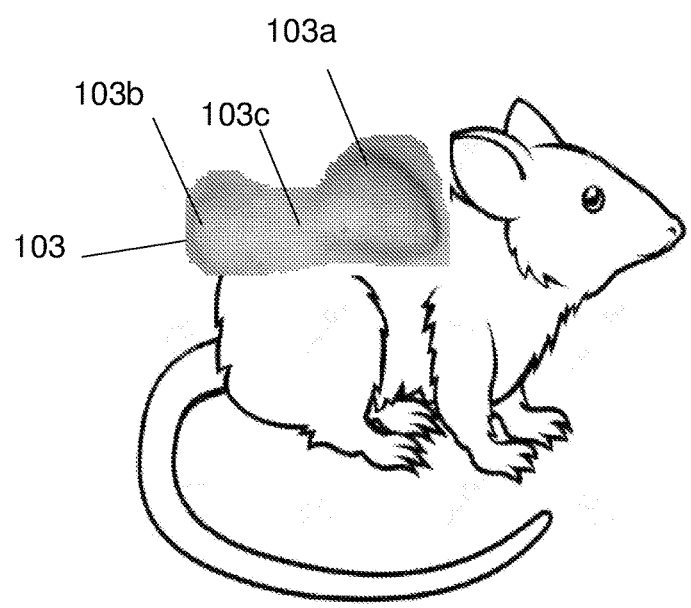

FIG. 1(c) shows diagrammatically how a double peak deformity 103 might present itself on the skin surface of a mammal, such as a rat or mouse. The edge of the deformity 103 is well-defined in some, but not all places, and the deformity 103 has two peaks 103a and 103b, and a flat region 103c between them. The curvature in the flat region is zero or close to zero. The curvature on the healthy skin surrounding the deformity is also zero or close to zero.

Figure 2A:
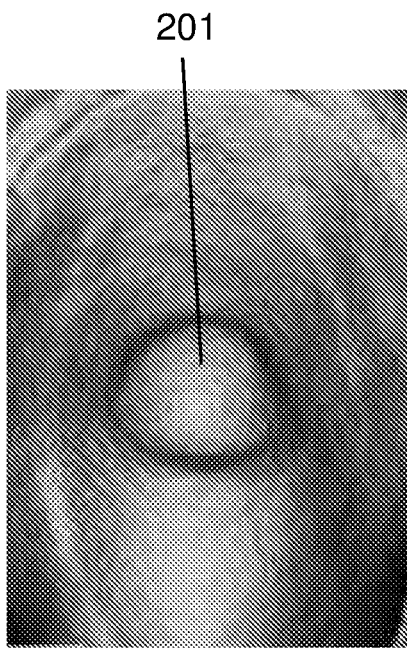
FIGS. 2(a)-(c) are images of the respective deformities of FIGS. 1(a)-(c) captured using a 3D imaging system.

FIG. 2(a) shows an image of the deformity 101 of FIG. 1(a). A single peak 201 is visible against the backdrop of the healthy, surrounding skin. Edge detection on this type of single peak 201 may generally be performed well with level-set method and other region growing algorithms.

Figure 2B:
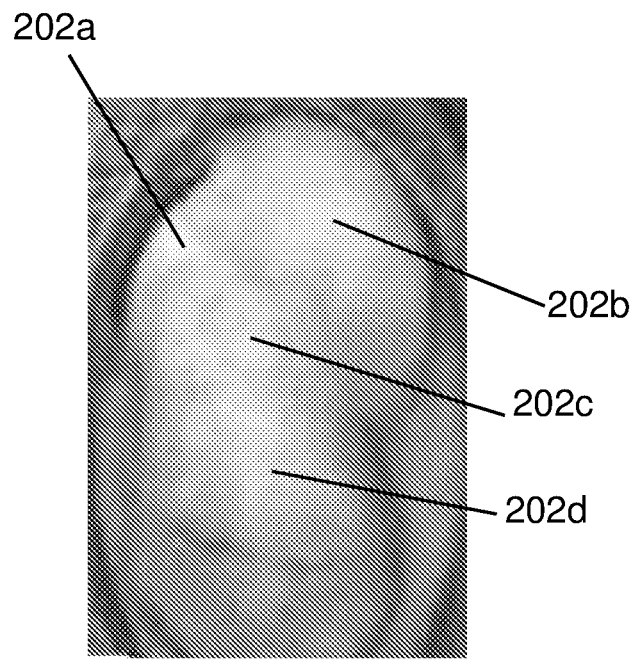

FIG. 2(b) shows an image of the deformity 102 of FIG. 1(b). Multiple peaks 202a-d are visible against the backdrop of the healthy skin. Edge detection on this type of multi-peak deformity using level-set method or region growing algorithms without data fusing, and/or peak splitting is prone to over or underestimation of deformity size.

Figure 2C:
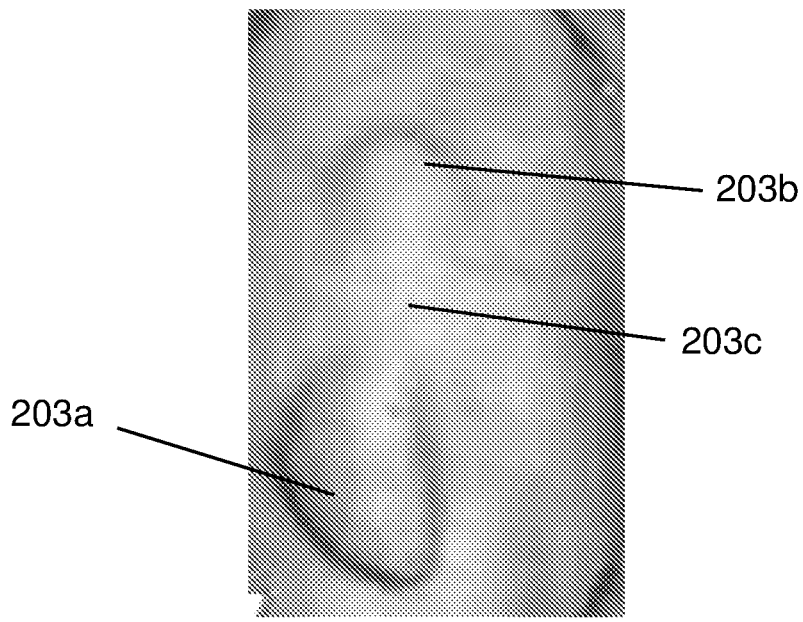

FIG. 2(c) shows an image of the deformity 103 of FIG. 1(c). Two peaks 203a, 203b are visible against the backdrop of the healthy skin. Edge detection on this type of double peak deformity using level-set method or other region growing algorithms without data fusing and/or peak splitting is prone to over or underestimation of deformity size. In particular, flat region 203c and the surrounding healthy skin have the similar curvatures.

Figure 3A:
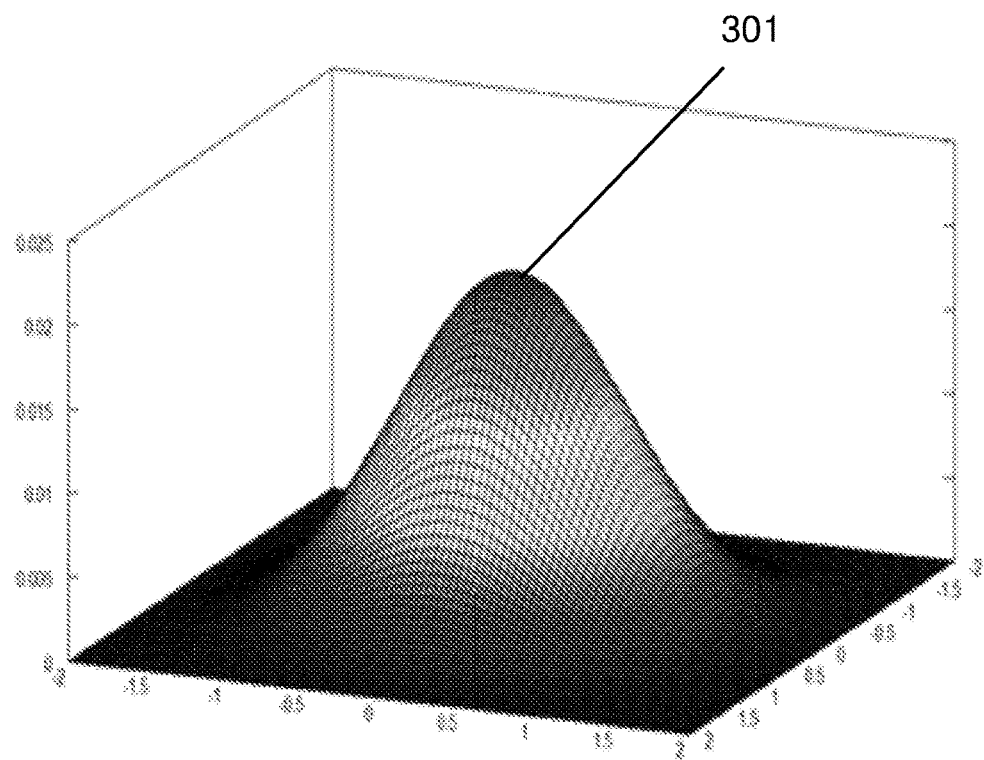
FIG. 3(a) is an illustrative graph of a depth map of a single peak deformity.

FIG. 3(a) shows an illustrative depth map generated from a 3D image of a single peak deformity. The tip of the peak 301 has significantly different depth and curvature values compared to the surrounding healthy skin.

Figure 3B:
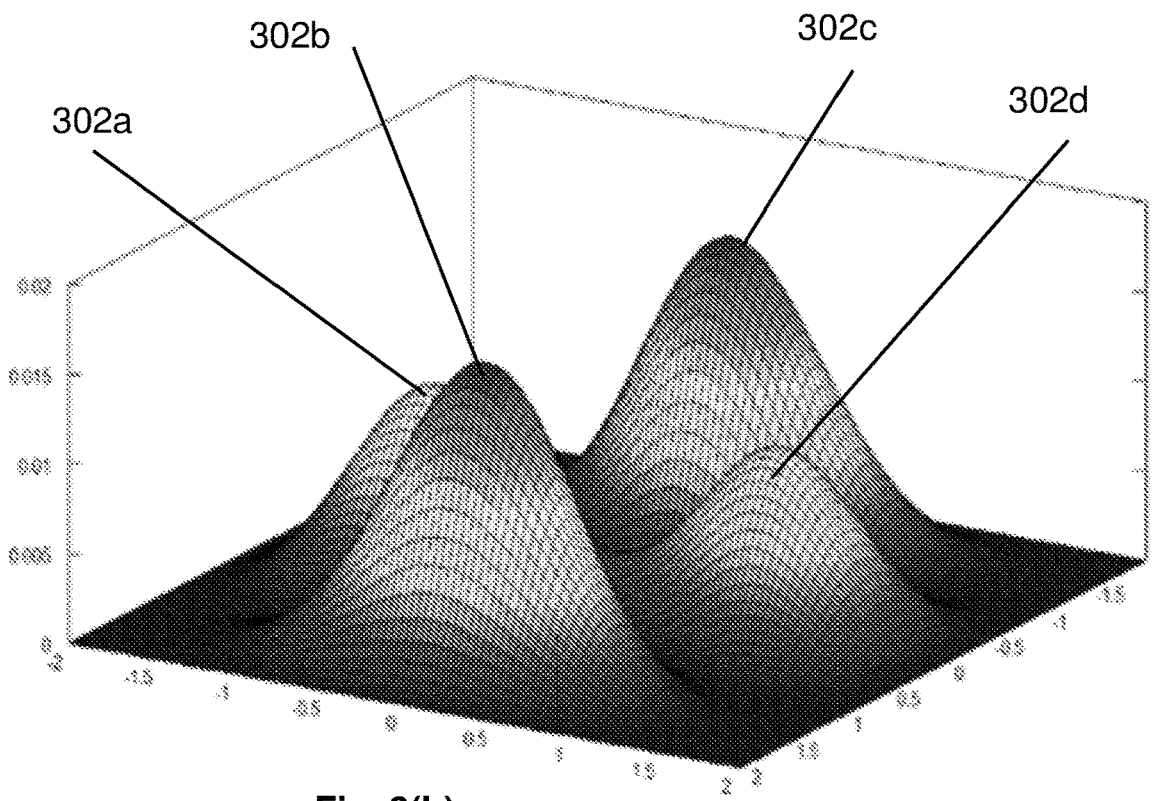
FIG. 3(b) is an illustrative graph of a depth map of a multi peak deformity.

FIG. 3(b) shows an illustrative depth map generated from a 3D image of a multi-peak deformity. The deformity has four peaks 302a-d of varying heights above the surrounding healthy skin. The surrounding healthy skin has zero curvature, as do many individual flat regions within the deformity. Determining which regions on this type of multi-peak deformity belong to the deformity rather than to the healthy surrounding skin using level-set method or region growing algorithms without data fusing and/or peak splitting is prone to over or underestimation of deformity size as the level-set method and other region growing algorithms do not always correctly determine termination conditions due to the number of low or zero curvature values at the flat regions within the deformity. Similarly, it is difficult to determine with many other region growing techniques whether a given pixel in these flat regions should be assigned to a deformity region or a background region, as the values associated with deformity pixels are so similar to background pixels.

Figure 4:
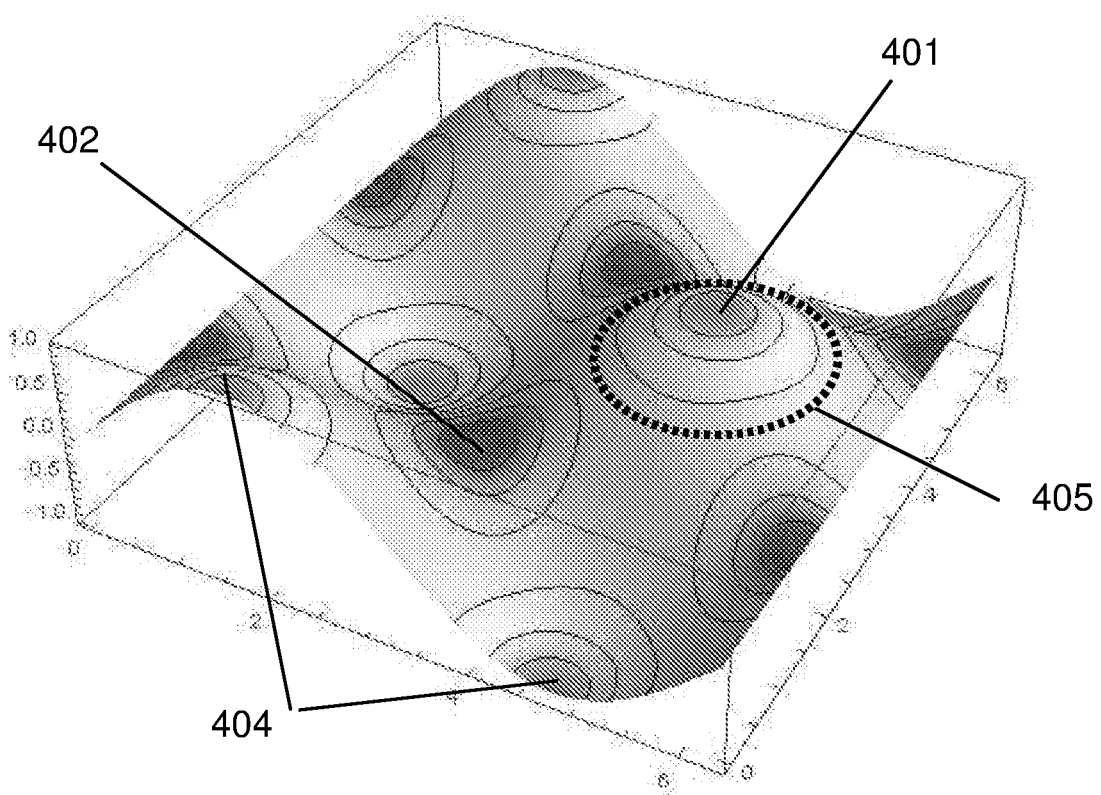
FIG. 4 is an illustrative graph of a curvature map of a multi peak deformity.

FIG. 4 shows an illustrative curvature map generated from a depth map of a multi-peak deformity. If the level-set method is performed taking peak 401 as a starting point, the low curvature point between saddle point 402 and peak 401 may cause the algorithms to detect termination conditions resulting in a deformity boundary shape indicated by dashed line 405. Other regions 404 which are still within the deformities actual boundary, are then missed and the algorithm output is an underestimation of the deformity's size.

Figure 5:
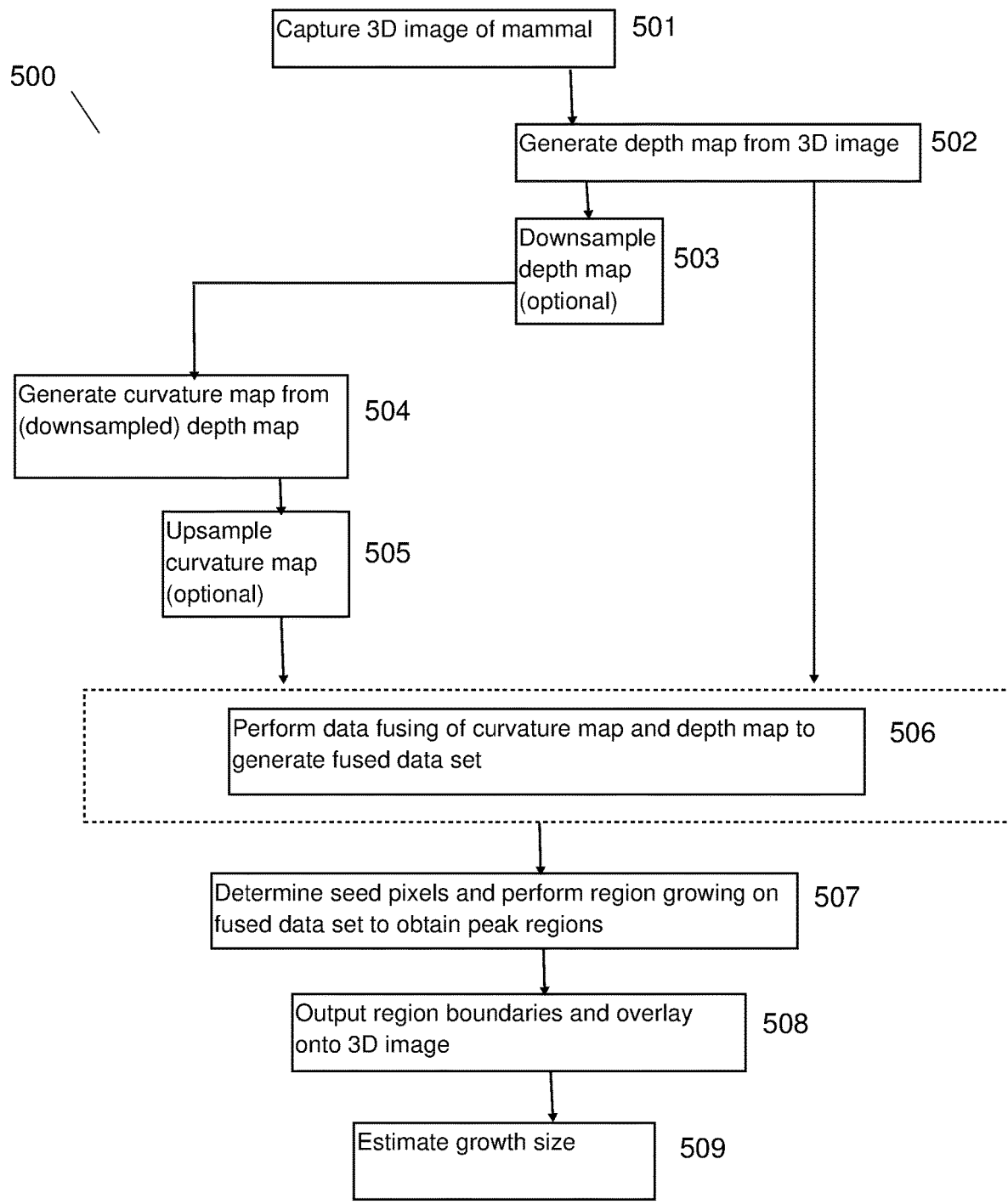
FIG. 5 is a flow diagram of a method which is an embodiment of the present invention.

Turning to FIG. 5, a method 500 is shown which is an embodiment of the present invention. It is performed on 3D image data by a processor. The processor may form part of a 3D imaging system used to capture the 3D image data, or it may be external to it, for example in the cloud.

In step 501, a 3D imaging system is used to capture a 3D image of a mammal, or a region of a mammal, such as a region of interest on the surface of the mammal's skin. The captured 3D image data includes the depth/height data of the imaged surface. It may be necessary to parse, normalise and format the data before further processing steps may be taken. For example, after the initial 3D image of the mammal has been captured, a region of interest (ROI) algorithm may be applied to the raw data to help to identify regions of interest and discard regions which are clearly not related to one or more of the peaks.

In step 502, a depth map is generated from the 3D image. The depth map associates (x,y) pixel coordinates with a (z) depth coordinate. The depth map may be separately outputted and colour coded (e.g. as a heat map). The depth map may also be normalised. The normalisation may be such as to ensure that the depth is non-zero at all points on the skin (e.g. all above zero or all below zero).

In optional step 503, the depth map is downsampled so as to decrease its resolution. The amount of downsampling required is dependent on the degree of computational efficiency required. Where the only available computing resources are those provided by an on-board processor of a 3D imaging system, a greater amount of downsampling may be required. Where greater resources are available for example through an on-demand, cloud-based CPU/GPU/TPU server farm, less or no downsampling may be necessary as computational efficiency in such a scenario is less of a priority. A multi-scale approach may be used to perform the downsampling. For example, a linear (Gaussian) scale-space representation of the depth map may be generated by performing a convolution of the depth map with a two-dimensional Gaussian kernel (i.e. effectively acting as a Gaussian filter). The parameters of the Gaussian kernel determine the level of smoothing, and thus the level of downsampling.

In step 504, a curvature map is generated from the optionally downsampled depth map. This may be performed using Gaussian curvature techniques, or any other suitable curvature techniques. The Gaussian curvature at each point of the imaged skin surface is the product of the principal curvatures at that point. Any suitable algorithm may be used to compute the Gaussian curvature at each point and thus to generate the curvature map. The curvature map associates the (x,y) pixel coordinates with a curvature value κ. The curvature map may be separately outputted and colour coded (e.g. as a heat map). The curvature map may also be smoothed and normalised.

In optional step 505, if optional step 503 has been performed, the curvature map is upsampled. Thus, where the curvature map has been generated from a downsampled depth map, the generated curvature map will have the same, lower resolution compared to the original depth map. In most cases, upsampling is required so as match the original, higher resolution of the non-downsampled depth map. If accuracy is not a priority, upsampling may be skipped and the method continued with both a downsampled depth map and a downsampled curvature map.

In step 506, the data fusing of the curvature map data and the depth map data is performed. The curvature map data includes a curvature value κ for each pixel coordinate, and the depth map data may include a depth value z for each pixel coordinate. As described above, the fused data set may be generated by applying at least one function to generate the fused data as at least one corresponding data value for each point on the skin which depends upon both the curvature map and the depth map, for example by applying the function $((a*\kappa)+(b*z))^2$ to each of the pixel coordinates to generate a fused data value f for each pixel coordinate. The set of fused data values f is denoted F. As described above, this function may be modified so as to emphasise either the curvature or the depth more in the fused data set, e.g. by a certain section of a and b, and/or by modifying the form of the function.

For pixels for which both the curvature and depth values are low, the fused value f will also be low. For pixels for which both the curvature and depth values are high, the fused value f will also be high. For pixels for which one of the curvature or depth value is high, the fused value f will be higher than for pixels where both the curvature and depth values were low. The fused data set may be outputted (e.g. plotted) and colour coded.

In step 507, region growing is performed on the fused data set F. This may be performed using any suitable region growing algorithm. In general, region membership criteria may be determined by generating a histogram of the fused data set F. Seed pixels and threshold f values may then be selected based on the histogram. For example, it may be apparent from the histogram what the highest f values (associated with peak tips) and lowest f values (associated with surrounding healthy skin) are, and thus which high f value pixels may be selected as seed pixels.

As described above, the initial seed regions may be automatically generated using the Otsu method. In particular, The Otsu method determines the optimal threshold in which the combined spread (i.e. intra-class variance) is either minimal or maximal. The threshold is then applied to the fused data set to generate seed regions associated with each peak.

Without data fusing, Otsu's method identifies very large numbers of potential initial seed regions, most of which are incorrect and not associated with peak regions. In particular, the optimal threshold (i.e. minimal or maximal combined spread) for a non-data fused set includes large numbers of pixels which should be identified as background pixels as belonging to foreground regions (e.g. imaging system artefacts, skin folds, hair, etc).

In contrast, with data fusing, Otsu's method identifies seed regions with a high degree of accuracy due to the effectively higher "contrast" between the background and foreground pixels.

As described above, the region corresponding to approximately 30% worth of peak height around the centres of each of the peaks may also be assumed to be part of and thus assigned to the deformity region, thus, in addition to automatically detecting seed regions using Otsu's method, the seed pixels may already define a region which includes a substantial part of the deformity surrounding the centre of the peak.

Region growing may be performed by using the level-set method as described above.

In step 508, the calculated region boundaries are outputted and may be overlaid onto the original image data to generate a composite image, which may be output from the system, e.g. to a screen.

In step 509, the outputs may be provided to a user (e.g. via the screen) who can assess the result and manually determine deformity size from the composite image. Alternatively, a suitable algorithm may be used to automatically calculate deformity size from the calculated region boundaries. By using an algorithm for this purpose, the human error in deformity size measurements may be entirely eliminated.

Although the numerical parameter of size has been described above, it is envisaged that the same methods may be applied to determine any other numerical characterisation parameter which may help to classify a deformity as belonging to one or more predetermined classes. For example, certain cancerous deformities are known to have a star-like shape. The shape is indicative of whether or not the deformity is malignant or benign. Thus the above described methods may determine the deformity boundary from which numerical characterisation parameters relating to its shape may be extracted (e.g. number of offshoots, regularity of the boundary, boundary symmetry etc), and thus from which the deformity may be classified as benign or malignant. In particular, cancerous deformities such as tumours may be classified as belonging to one of five types and it is envisaged that the above described methods may be used to classify the type to which the tumour belongs by extracting one or more indicative numerical parameters enabling classification of the deformity into one or more predetermined classes.

Figure 6:
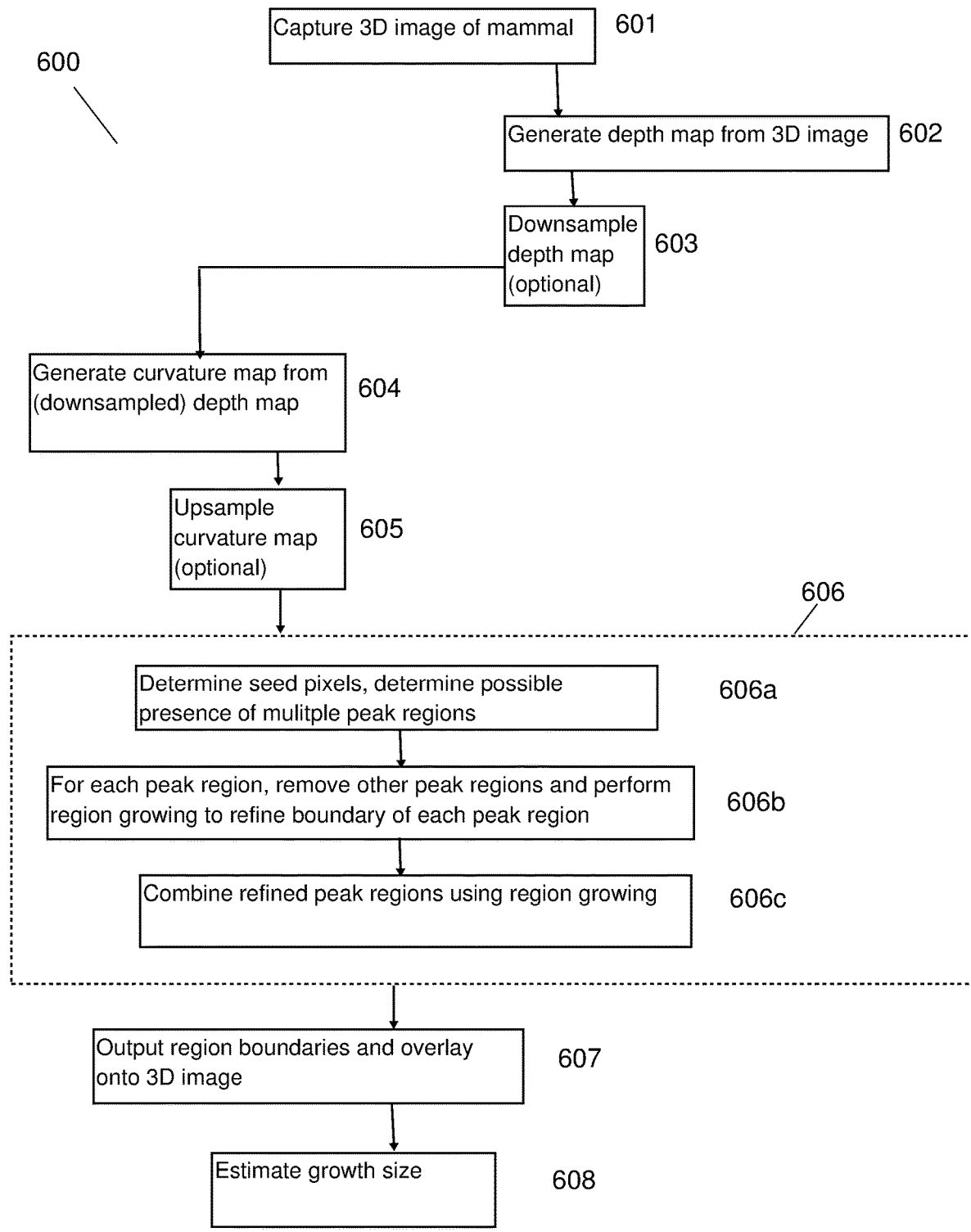
FIG. 6 is a flow diagram of a method which is an embodiment of the present invention.

Turning to FIG. 6, a method 600 is shown which is an embodiment of the invention. It is performed on 3D image data by a processor. The processor may form part of a 3D imaging system used to capture the 3D image data, or it may be external to it, for example in the cloud. Method 600 may be used alone, or in conjunction with method 500. The steps of method 600 which are the same as method 500 are described only briefly below but the same considerations as described above in relation to method 500 apply.

In step 601 a 3D imaging system is used to capture a 3D image of a mammal.

In step 602, a depth map is generated from the 3D image.

In optional step 603, the depth map may be downsampled.

In step 604, a curvature map is generated from the optionally downsampled depth map.

In optional step 605, the curvature map is upsampled (if it had previously been downsampled).

The same pre-processing steps of ROI generation, parsing, normalising and formatting the data may also be performed.

In step 606a, seed regions are determined using, for example, Otsu's method as described above.

In some embodiments, Where Otsu's method results in potentially multiple peak regions, each is considered in turn.

If the peak region under consideration is the first to be considered, a distance transform may be performed on its constituent pixels and a convex hull generated which encloses these pixels. The convex hull provides a mask indicating an initial estimate of the boundary of the first peak region.

The next peak region is then considered and a convex hull is similarly generated around its constituent pixels, thereby also providing a mask indicating an initial estimate of the boundary of the second peak region.

In some instances, the two convex hull masks may overlap. Where this is the case, it is necessary for the algorithm to check whether or not the peak region associated with the second convex hull mask is in fact simply an extension of the peak region associated with the first convex hull mask. This may be the case, for example, where the first convex hull mask is entirely within the second convex hull mask. Thus, the peak region associated with the first convex hull mask is extended to the boundary of the second convex mask, and the second peak region rejected as it is not in fact a separate peak.

If the second convex hull mask is determined not to be an extension of the first convex hull mask, then a similarity value between the pixel values in each region is determined (e.g. by determining the mean pixel value of both regions and comparing them). If the similarity value indicates the peak regions are similar, then the second convex hull mask is accepted as a separate peak. If not, the peak is rejected.

The same process may be performed iteratively until all of the seed regions have been accepted or rejected. If it is known that the deformities under consideration (such as certain types of tumours) only ever present with up to three peak regions, then the process may continue until the number of accepted/rejected peaks is three.

In step 606b, region growing is performed separately on each of the accepted peak regions. This may be achieved by removing the other peak regions from the data during region growing. The output of this step is a plurality of distinct peak regions whose boundaries have been refined by region growing. As described above, region growing on single peak regions is more accurate than region growing simultaneously on multiple peak regions.

In step 606c, the distinct, refined peak regions output in step 606b are recombined. In some embodiments this may be achieved by generating a convex hull mask around the pixels of the refined peak regions and performing region shrinking for the pixels inside the mask and contiguous with the peak regions. The result is the generation of a bridging region between two or more distinct regions.

Alternatively, a thin strip of pixels extending directly between the centre pixels of the regions may be selected as a starting region, and the bridging region grown outwards using region growing.

Any other suitable region growing or region shrinking methods may be used to generate the bridging region.

In step 607, the calculated region boundaries are outputted and may be overlaid onto the original image data to generate a composite image, which may be output from the system, e.g. to a screen.

In step 608, the deformity size may be estimated. As with method 500, the region boundaries of the deformity as a whole may be outputted and provided to a user (e.g. via a screen) who can assess the result and manually determine deformity size. Alternatively, a suitable algorithm may be used to automatically calculate deformity size from the calculated region boundaries. By using an algorithm for this purpose, the human error in deformity size measurements may be entirely eliminated.

Similarly to method 500, any other numerical parameter may also be extracted so as to classify the deformity as belonging to one or more predetermined classes.

Turning to FIGS. 7(a)-(e), a series of images are shown of the deformity of FIG. 1(c) at different stages of being processed according to method 600. FIG. 7(a) shows the original image data of the deformity of FIG. 1(c). In FIG. 7(b) shows an output of a region growing algorithm which has been performed on a curvature map calculated from the depth map of the deformity shown in FIG. 7(a). FIG. 7(b) shows that region growing resulted in at least three regions: background region 701, a first peak region 702, and a second peak region 703. Some background noise artefacts are also present. These may be removed using any suitable noise reduction or image processing technique. In FIG. 7(c), the background noise has been removed and a convex hull model has been used to generate a curve wrapping around the first peak region 702 and the second peak region 703, to define a contiguous "inside" bridging region 704 which may be used as a basis for region shrinking. In FIG. 7(e), region shrinking has been applied to inside region 704 using suitable region membership criteria e.g. based on depth and/or curvature. Where data fusing has been performed beforehand, region membership criteria may be based on f values from the fused data set F. The resultant region provides an accurate indication of the boundaries of the deformity of FIG. 1(c), from which its size and/or other numerical characterisation parameters can be extracted. For example by analysing the data manually or with a suitable algorithm. FIG. 7(e) shows the resultant deformity region overlaid onto the originally captured image.

Figure 8:
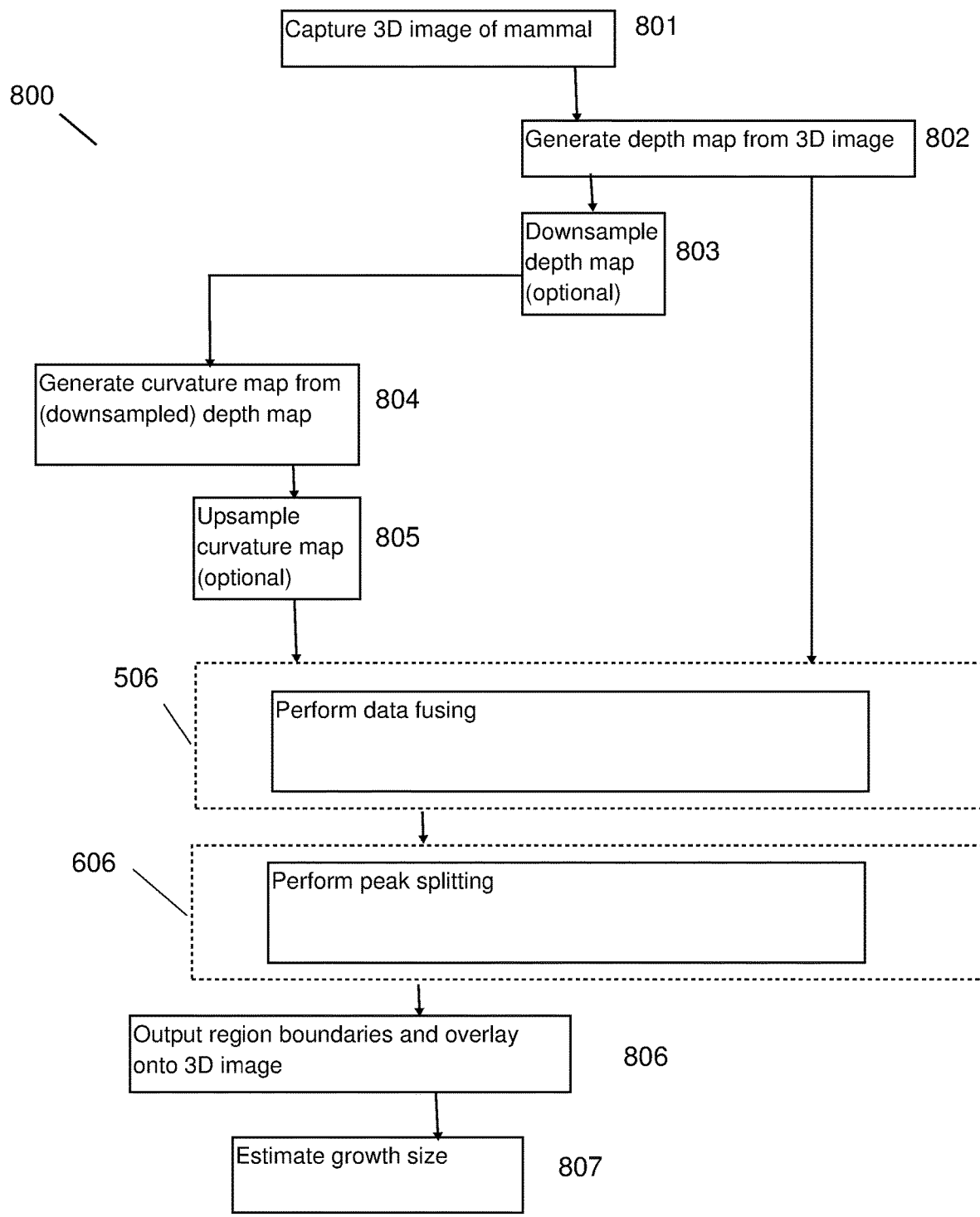
FIG. 8 is a flow diagram of a method which is an embodiment of the present invention.

Turning to FIG. 8, a method 800 is shown which is performed on 3D image data by a processor. The processor may form part of a 3D imaging system used to capture the 3D image data, or it may be external to it, for example in the cloud. Method 800 uses a number of the steps from methods 500 and 600 in conjunction. The steps of method 800 which are the same as methods 500 and 600 are described only briefly below but the same considerations as described above in relation to methods 500 and 600 apply.

In step 801 a 3D imaging system is used to capture a 3D image of a mammal.

In step 802, a depth map is generated from the 3D image.

In step optional step 803, the depth map may be downsampled.

In step 804, a curvature map is generated from the optionally downsampled depth map.

In step optional step 805, the curvature map is upsampled (if optional step 803 had been performed).

Step 506 of method 500 is then performed on the curvature map generated in step 805. The output is a fused data set. Step 606 from method 600 is then performed on the fused data set to identify peak regions and background regions, and to combine the peak regions using, for example, a convex hull model and region shrinking, or region growing on a strip of pixels between the peak regions, or any other suitable bridging region generation technique.

In step 806, the calculated region boundaries are outputted and may be overlaid onto the original image.

In step 807, the deformity size or other numerical characterisation parameters are estimated in the same way as in methods 500 and 600.

Whilst the foregoing description has described exemplary embodiments, it will be understood by those skilled in the art that many variations of the embodiment can be made within the scope of the attached claims. For example, although the present invention has been described in relation to deformity detection in mammals, it may also be used for the same purpose with other animals, such as reptiles and birds.

In a variation of the method 800, the data fusing step 506 and peak splitting step may be performed the other way around (i.e. peak splitting first, and data fusing second). This may be advantageous where the data fusing process generates excessive image processing artefacts during the image segmentation step.

The above described methods have been described as being performed by a processor on-board or external to a 3D imaging system. Such a processor may execute instructions, codes, computer programs, scripts which it accesses from hard disk, floppy disk, optical disk (these various disk based systems may all be considered secondary storage), flash drive, ROM, or RAM. Multiple processors may be present.

Thus, while instructions may be discussed as executed by a processor, the instructions may be executed simultaneously, serially, or otherwise executed by one or multiple processors.

The above described methods have been described in relation to using region growing to determine region boundaries and thus estimate deformity size. In some embodiments, region growing may be reformulated as a problem to be solved by a deep learning convolutional neural network. Thus a convolutional neural network may be trained to grow a region. The data which has undergone data fusing and/or peak splitting may then be inputted into the trained network to obtain estimations of the region which defines a deformity edge the peak edge(s).

The above described methods have been described as being advantageous to overcoming difficulties in estimating the boundaries of a region of skin which defines multi-peak deformities. However, data fusing may also be used to improve the accuracy of estimating boundaries of regions which define single peak deformities, as the data fusing step results in the effective contrasts in the fused data set becoming exaggerated and thus resulting in each pixel being more easily assigned to a background or peak region. Further, peak splitting may also be used to improve the accuracy of estimating regions made up of other features which present as separate shapes on the skin surface. For example, peak splitting may also be used to more accurately estimate scar tissue size, wound/cut size, rash size, pustule/blister size, and/or any other skin surface feature that may need to be sized.

The above described methods have been described in relation to deformities which protrude from above the surface of the skin. However, all of the above methods may equally be used to estimate a region associated with any other deformity, including a cavity which dips into the surface of the skin. Thus the above described methods provide a method for estimating a region associated with a deformity on or under a surface portion of the skin.

Although the above described methods have been described using depth and curvature, and one data fusion step, it is envisaged that additional data types and additional data fusion steps may be performed to further increase the advantages provided by data fusion. For example, depth, Gaussian curvature and Normal curvature may be fused using a suitable function, such as $((a*\kappa_G)+(b*z)+(c*\kappa_N))^2$ where a, b, and c are constants, $\kappa_G$ is the Gaussian curvature, z is the depth and $\kappa_N$ is the Normal curvature. The fused data set will thus comprise a fusion of at least three data sets. In other possibilities, one of the data sets may describe a colour of respective points on the skin, the normal direction to respective points on the skin (or the departure of the normal direction from a corresponding point of a model of the skin the absence of the deformity), or any other parameter describing the skin (e.g. the measured temperatures of respective points of the skin).

In particular, the above described methods have been described in relation to using depth (i.e. height above or below the surface of the skin) and curvature values derived from depth. However, the same methods may equally be applied to any other data associated with pixel coordinates of a captured image. For example, a temperature sensitive imaging system may capture a temperature map of the imaged surface. There may be "peaks" of higher and/or lower temperatures which may or may not be associated with the same deformity. The boundaries of the regions associated with these higher or lower temperature "peaks" may thus be more easily determined and the deformity classified as belonging to one or more predetermined classes. For example, the boundaries of a cancerous growth with many blood vessels may be more easily detected from surface imaging by fusing depth and/or curvature with temperature (e.g. because more blood vessels may generate more heat). Indeed it is envisaged that the above described methods may be used in relation to any data which may be associated with pixel coordinates and in which "peaks" are apparent in the data. Such peaks would not be physical peaks defined by the height above or below the surface of the skin, but rather peaks in data values. This type of other data may have been captured by means such as, for example, medical imaging systems which obtain X-ray data, CT-scan data, ultrasound scan data, MRI scan data and/or any other under the skin visualisation data. For example, depth and curvature data may be fused with ultrasound scan data. This may be particularly useful where information from under the surface of the skin has an impact on how the deformity presents on the surface of the skin, thus further improving accuracy of seed region generation and region growing. Surface colour and texture may also be used as a data type for data fusion.

Otsu's method has been described above as being unexpectedly advantageous when performed on the fused data to generate seed regions given the effective increase in "contrast" that is present in the fused data set. However, other seed region generation techniques may also be used on the depth, curvature, fused data and/or other types of data to determine initial seed regions, and to determine a stopping criteria for the region growing algorithms.

The invention claimed is:

1. A method for estimating a region associated with a deformity on or under a surface portion of the skin of a mammal, the method comprising: capturing an image of the surface portion to produce first data; generating second data from the first data; combining the first data and the second data to produce third data; and performing image segmentation on the third data to identify a region of interest portion of the image, wherein performing image segmentation on the third data comprises performing region growing on the third data, wherein the step of region growing comprises, with the first, second and/or third data, selecting a group of one or more pixel coordinates as a seed point or region and, with the first, second and/or third data, selecting a threshold value as a stopping criteria; wherein the image is a three-dimensional image, the first data comprises depth data, and the second data comprises surface curvature data.

2. A method according to claim 1, wherein the first data and the second data comprise pixel coordinates of the three-dimensional image; and wherein the step of combining the first data and the second data comprises applying a function to the first data and the second data.

3. A method according to any preceding claim, wherein when the deformity has a first peak and a second peak, said region of interest portion of the image comprises a first region associated with the first peak and a second region associated with the second peak; and the method comprises combining the first region and the second region.

4. A method according to claim 3, wherein the step of combining the first region and the second region comprises: generating a convex hull around the first region and the second region; and refining a boundary of said convex hull.

5. A method according to claim 4, wherein said step of refining a boundary of said convex hull comprises performing region shrinking on the convex hull.

6. A method for estimating a region associated with a deformity on a surface portion of the skin of a mammal, the deformity having a first peak and a second peak, the method comprising: capturing a three-dimensional image of the surface to produce first data that comprises depth data; generating modified data from the first data to generate second data comprising curvature data, wherein the first data and the second data comprise data values for each of a plurality of pixels of the three-dimensional image; performing image segmentation on the modified data to identify a region of interest portion of the image, the image segmentation comprising identifying a first region associated with the first peak and identifying a second region associated with the second peak, the image segmentation further comprising performing region growing on the modified data, the region growing comprising, with the second data, selecting a group of one or more pixels as a seed point or region and, with the second data, selecting a threshold value as a stopping criterion; and combining the first region and the second region.

7. A method according to claim 6, wherein the step of combining the first region and the second region comprises: generating a convex hull around the first region and the second region; and refining a boundary of said convex hull.

8. A method according to claim 6, wherein said step of refining a boundary of said convex hull comprises performing region shrinking on the convex hull.

9. A method according to any of claims 1 to 2 or 3 to 5, wherein the step of generating the second data comprises calculating Gaussian curvature or Normal curvature of the first data.

10. A method according to any of claims 1 to 2 or 3 to 5, comprising downsampling the first data before generating the second data; and upsampling the second data.

11. A method according to claim 10, wherein the steps of downsampling and upsampling comprise using a multi-scale approach.

12. A method according to any preceding claim, comprising estimating at least one numerical characterisation parameter of the deformity.

13. A method according to claim 12, wherein the deformity belongs to one or more predetermined classes, and said method comprises classifying the deformity as belonging to one or more of said predetermined classes using said at least one numerical characterisation parameter.

14. A method according to claim 12 or 13, wherein said at least one numerical characterisation parameter comprises a volume of the deformity, and wherein said step of estimating the at least one numerical characterisation parameter comprises estimating said volume using: the first data, and an output of the step of performing image segmentation.

15. A method according to any preceding claim, wherein the step of performing image segmentation is performed by a convolutional neural network.

16. A method according to any preceding claim, wherein the step of capturing said image comprises using at least one of stereoscopy and photometry.

17. A non-transitory data carrier carrying processor control code to implement the method of any one of preceding claim.

18. An imaging system having at least one image device and a processor operative to implement the method of any one of claims 1 to 16.

* * * * *